United States Patent
Stamile et al.

(10) Patent No.: US 9,468,377 B2
(45) Date of Patent: Oct. 18, 2016

(54) PORTABLE MEDICAL DEVICE AND METHOD FOR QUANTITATIVE RETINAL IMAGE ANALYSIS THROUGH A SMARTPHONE

(71) Applicant: Università della Calabria, Rende (IT)

(72) Inventors: Claudio Stamile, Rende (IT); Renato Umeton, Rende (IT); Michele Cavallari, Rende (IT); Francesco Calimeri, Rende (IT); Francesco Orzi, Rende (IT)

(73) Assignee: UNIVERSITÀ DELLA CALABRIA, Rende (IT)

( * ) Notice: Subject to any disclaimer, the term of this patent is extended or adjusted under 35 U.S.C. 154(b) by 38 days.

(21) Appl. No.: 14/294,171

(22) Filed: Jun. 3, 2014

(65) Prior Publication Data
US 2015/0320313 A1    Nov. 12, 2015

(30) Foreign Application Priority Data

May 8, 2014 (IT) .............................. CS2014A0017

(51) Int. Cl.
*A61B 3/14* (2006.01)
*A61B 3/00* (2006.01)
*A61B 3/12* (2006.01)
*G06T 7/00* (2006.01)

(52) U.S. Cl.
CPC .............. *A61B 3/14* (2013.01); *A61B 3/0008* (2013.01); *A61B 3/12* (2013.01); *G06T 7/0012* (2013.01); *G06T 7/0081* (2013.01); *G06T 7/0091* (2013.01); *G06T 2207/10024* (2013.01); *G06T 2207/20044* (2013.01); *G06T 2207/20144* (2013.01); *G06T 2207/30041* (2013.01)

(58) Field of Classification Search
CPC ........ A61B 3/10; A61B 3/1233; A61B 3/14; A61B 3/145
USPC ........ 351/205, 206, 210, 216, 218, 245, 246
See application file for complete search history.

(56) References Cited

U.S. PATENT DOCUMENTS

| | | | | |
|---|---|---|---|---|
| 2014/0049636 A1* | 2/2014 | O'Donnell | ............. | G08C 17/02 348/143 |
| 2014/0063292 A1* | 3/2014 | Wagner | ................. | G01N 21/87 348/231.99 |

FOREIGN PATENT DOCUMENTS

WO    WO 2015/071779    *    5/2015    ............... A61B 3/14

* cited by examiner

*Primary Examiner* — Huy K Mai
(74) *Attorney, Agent, or Firm* — Mark M. Friedman

(57) ABSTRACT

The present invention essentially consists of an integrated system that allows acquisition and quantitative analysis of high-resolution images of the retina. The integrated system includes an optical device and a software app. The optical device is a smartphone-adapted lens for acquisition of high-resolution images of the retina. The software app is a smartphone app for quantitative analysis of the retinal images acquired through the hardware component of the device. The computation is carried out by means of cloud-based technologies. Quantitative indices of retinal damage are obtained. These indices are proven for being relevant for both clinical and research purposes.

15 Claims, 3 Drawing Sheets

Adjustable band (3D view)

Lens/Refractor support (Frontal View)

Fig. 1 – Adjustable band (3D view)

Fig. 2 - Lens/Refractor support (Frontal View)

Fig. 3 – Refractor (Lateral Section)

Fig. 4 – Lens/Refractor support applied to the smartphone

Fig. 5 - Workflow

PORTABLE MEDICAL DEVICE AND METHOD FOR QUANTITATIVE RETINAL IMAGE ANALYSIS THROUGH A SMARTPHONE

TECHNICAL FIELD

The innovation herewith presented refers to the technical field of portable medical devices. Specifically, the innovation consists in a portable medical device that allows acquisition and analysis of retinal images through a mobile device, such as a smartphone.

STATE OF THE ART

Examination of the retina through fundoscopy is a key medical procedure for diagnosis and monitoring of a number of pathological conditions, including ophthalmologic (e.g. glaucoma and macular degeneration), endocrinologic (e.g. diabetes), cardiovascular (e.g. hypertension) and neurologic disorders (e.g. brain tumors, head trauma, cerebrovascular diseases, dementia and multiple sclerosis). However, full exploitation of fundoscopy in clinical settings is currently quite limited due to two main reasons:

acquisition of retinal images mostly relies upon expensive and non-portable devices;

analysis of retinal images is limited to qualitative, naked-eye assessment of retinal abnormalities in routine clinical practice.

In the last decade, a number of devices and software tools have been developed to answer the needs for improving acquisition and analysis of retinal images. However, these solutions succeeded in improving either portability or analysis, neglecting to integrate the innovations and thus to obtain an inexpensive, portable technology that addresses both needs.

To date, a few innovations have been developed in order to acquire retinal images through a portable device, such as a smartphone; however, it is worth noting that none of them is coupled with a software that performs quantitative analyses of the images.

A few commercial adapters have been developed to connect smartphones to a slit-lamp or a portable ophthalmoscope: examples of these technologies are Magnifi (www.arcturuslabs.com), Orion SteadyPix Telescope Photoadapter (www.telescope.com), EyePhotoDoc (www.EyePhotoDoc.com), Keeler Portable Slit Lamp Adapter (www.keelerusa.com), iExaminer (www.welchallyn.com), Zarf Adapter (www.zarfenterprises.com). All of them feature only acquisition and storage of retinal images, and require an ophthalmoscope to be functional. Similarly, the method described by Haddock et al. [1] allows acquisitions, yet not quantitative analyses, of high-definition images or movies of the retina using a smartphone and an external lens. Two recent inventions developed by eyeNETRA (www.eyenetra.com) make use of smartphone apps and an external hardware device to measure visual acuity or assess cataracts.

It is worth stating that none of the abovementioned technologies perform quantitative image analysis of the retina.

The recent development of digital imaging techniques and cloud computing has provided us with impressive capabilities for storage, transfer and quantitative analyses of the retinal images, and paves the way to quantitative approaches rather than observer-driven evaluations. In the last decade, several computer-assisted methods have been developed for the automation the analysis of the retinal images. These approaches are being employed in clinical practice as well as in clinical and research studies, in order to evaluate the retinal damage in patients suffering from most of the pathologic conditions listed above. Measurements of retinal vessel diameter—usually expressed as arteriolar-to-venular ratio (AVR)—as well as quantitative assessments of the retinal vessel architecture via indices of tortuosity and fractal analysis are fundamental targets of these approaches.

Probably, the most largely employed method is the one by Hubbard et al. [2], which was recently incorporated into a commercial software package known as Singapore I Vessel Assessment (SIVA). This software allows simultaneous analyses of the diameter, tortuosity and fractal dimension of the retinal vessels, and has been validated by clinical studies [3]. However, this technology is available only for workstations.

While a number of portable instruments were developed for acquisition of retinal images and softwares were developed for image analysis, none of the available tools integrate, within a single, inexpensive, portable device (such as a smartphone), both improved acquisition and quantitation of the retinal image.

The herein presented invention provides an integrated tool, which improves both fundoscopy acquisition and retinal image analysis.

The originality of the presented tool can be appreciated by examining the similar, available devices. iExaminer (www.welchallyn.com) can be considered the closest device to the present invention. iExaminer is an adapter system that connects a smartphone to a portable ophthalmoscope. A smartphone app to store the acquired retinal images and patients' information is also provided. As a major limitation, iExaminer does not perform any quantitative analysis of the retinal images. Furthermore, the adapter system is relatively cumbersome.

The present invention consists of an optical device and a software, both suitable for a smartphone. The optical device is a macro lens to be mounted on the smartphone body to acquire retinal images. The software computes quantitative indices of retinal damage.

The main innovation is the integration of the hardware and software in a single tool. The result is a portable, inexpensive device for acquisition and quantitative analysis of retinal images. The software is also innovative per se, both for being engineered as a smartphone app and for performing innovative, advanced quantitative analyses of parameters concerning the morphology of the retinal vessels trees. We indeed developed a retinal image analysis software that performs unmatched measurements of clinically relevant indices of retinal damage. It is worth mentioning that the tool has been validated in a clinical study [4]. The software allows us to discriminate pathological conditions characterized by morphological changes of retinal vessels, such as hypertensive retinopathy and cerebrovascular disease. The software has been engineered and properly incorporated into a powerful smartphone app.

The effective integration of smartphone+lens+app results in a truly innovative solution, which combines an extremely portable and inexpensive hardware for the acquisition of retinal images with a software that performs quantitative analyses of clinically relevant parameters on the acquired images of the retina.

SUMMARY OF THE INVENTION

The present invention essentially consists of an integrated system that allows acquisition and quantitative analysis of high-resolution images of the retina. The integrated system includes an optical device and a software app. The optical device is a smartphone-adapted lens for acquisition of high-resolution images of the retina. The software app is a smartphone app for quantitative analysis of the retinal images acquired through the hardware component of the device. The computation is carried out by means of cloud-based technologies. Quantitative indices of retinal damage are obtained. These indices are proven for being relevant for both clinical and research purposes.

BRIEF DESCRIPTION OF THE DRAWINGS

Various embodiments are herein described, by way of example only, with reference to the accompanying drawings, wherein.

DESCRIPTION OF A PREFERRED EMBODIMENT OF THE INVENTION

The present invention consists in an optical device for the acquisition of high-resolution retinal images through a smartphone equipped with camera and a light source, where the acquired images will be processed by the smartphone app in order to obtain quantitative indices of retinal damage.

Figure 1:
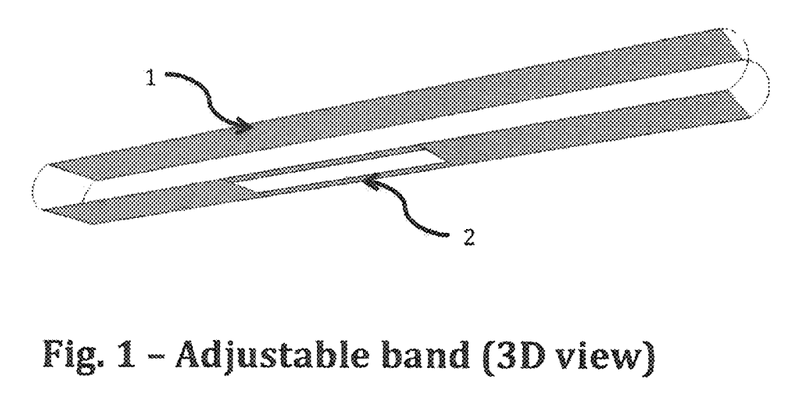
FIG. 1 is an isometric view of the adjustable band of the immediate invention.
Figure 2:
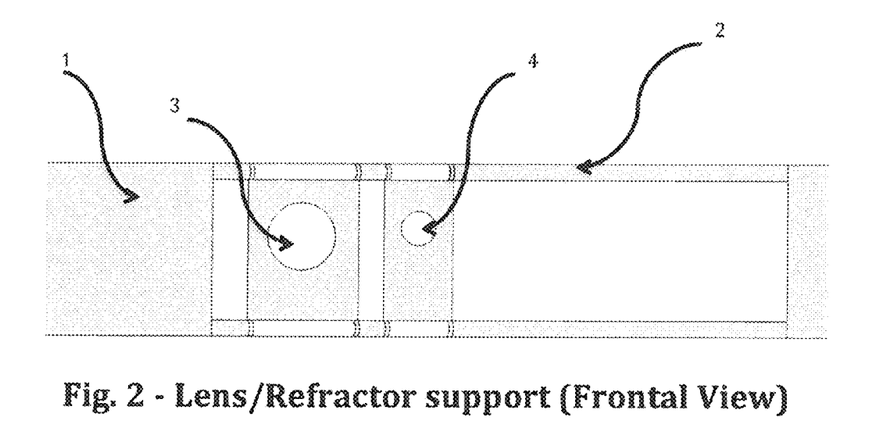
FIG. 2 is a frontal view of the lens and refractor support.
Figure 4:
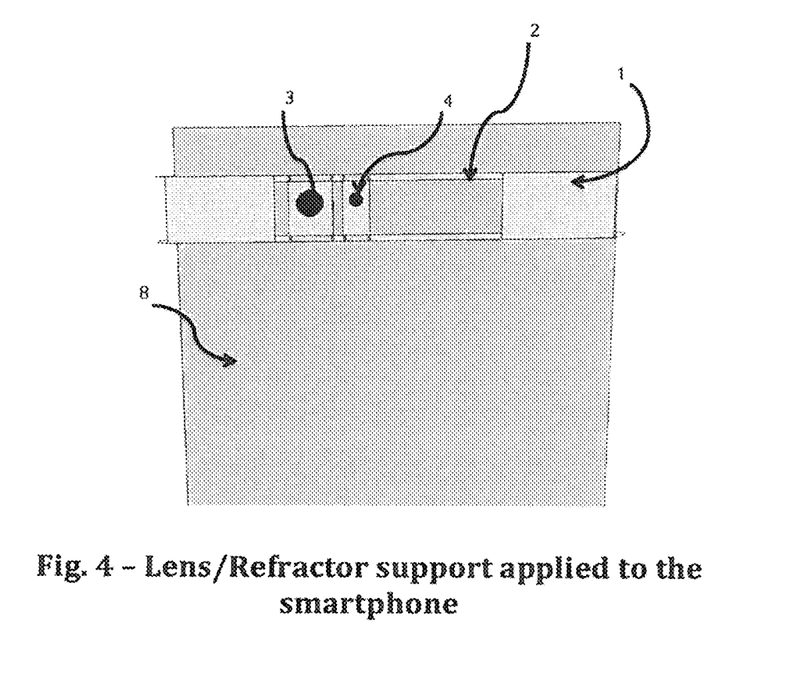
FIG. 4 is a frontal view of the lens and refractor support applied to a smartphone.

The optical device includes:
smartphone (8), FIG. 4;
adjustable band (I), FIG. 1, with a built-in sliding track (2), FIG. 1;
lens (3), FIG. 2;
refractor (4), FIG. 2.

The adjustable band (1), FIG. 1, is mounted on the smartphone (8), FIG. 4 to allow the positioning of the lens (3), FIG. 2 and refractor (4), FIG. 2, in front of the smartphone's camera and flash light, respectively. The adjustable band (1), FIG. 1, mounted on the smartphone body (8), FIG. 4 is represented in FIG. 4.

The lens (3), FIG. 2—and the refractor (4), FIG. 2, are mounted on the sliding track (2), FIG. 1, of the adjustable band (1), FIG. 1, next to each other (3,4) FIG. 2. By means of the built-in sliding track on the adjustable band (1), FIG. 2 the position of the lens (3), FIG. 2, and refractor (4), FIG. 2, can be adjusted to face the camera and the light source of the smartphone.

Figure 3:
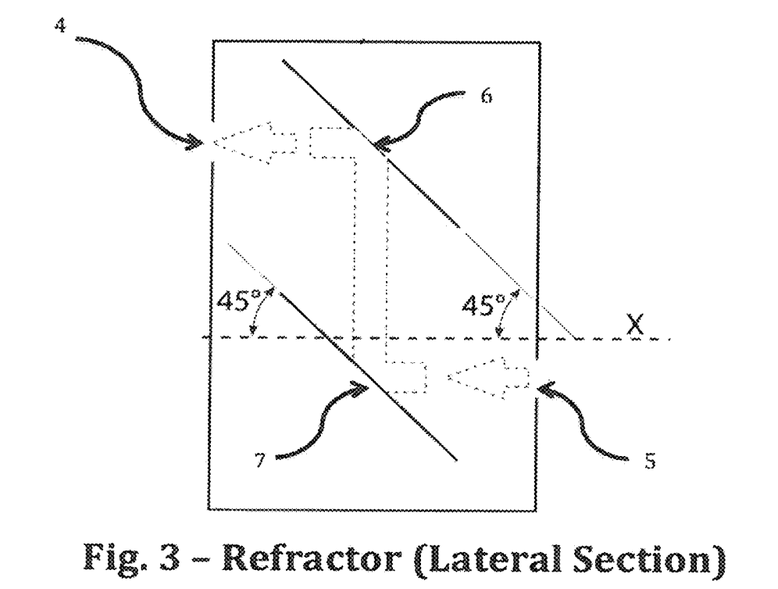
FIG. 3 is a lateral view of the inner structure of the refractor.

The inner structure of the refractor, as it can be seen in FIG. 3, includes two rectangular parallel mirrors (6,7), which are positioned at a 45-degree angle with respect to an axis perpendicular to the surface of the refractor. An input hole (5), FIG. 3, allows the light coming from the light source of the smartphone to get into the refractor. An output hole (9), FIG. 3, allows the refracted light to gather through the corneal window into the pupil and shine the inner posterior surface of the eye bulb, which corresponds to the retina. Once the retina has been brightened with light, a photo of the retina can be acquired through the smartphone camera and lens system.

The lens (3), FIG. 2 is a macro calibrated to focus on the retina. Once a retinal image has been acquired, it is temporarily stored and sent to a processing module through the smartphone app.

The smartphone app performs the analysis of the retinal images acquired through the optical device described above. The analysis workflow performed by the smartphone app includes:

1. automated detection of optic nerve abnormalities, such as papilledema or optic neuritis;
2. computation of the following three indices, which were proved to reflect retinal vessel damage:
    Arteriole-to-Venule Ratio (AVR), based on vessel diameter measurements averaged along a vessel segment (as opposed to measurements obtained on a single, arbitrarily chosen vessel point);
    Tortuosity Index (TI), a measure of swinging or twisting of the vessels;
    Mean Fractal Dimension (Mean-D), an index of complexity or density of the retinal vessel branching.

Figure 5:
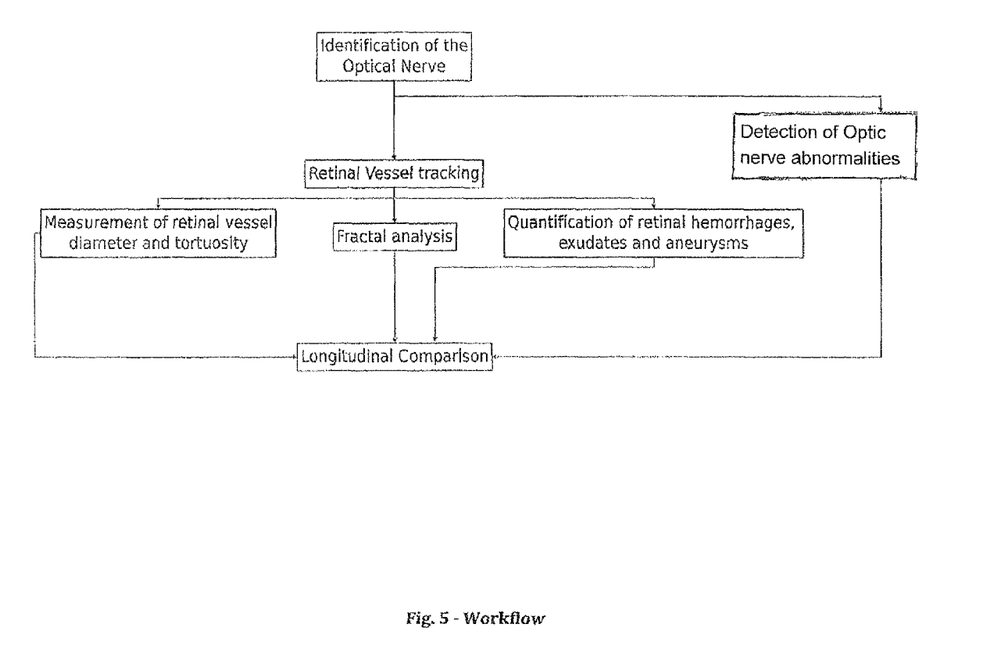
FIG. 5 is a workflow diagram of the macro-phases performed by the software to measure the size of the retinal hemorrhages, exudates or aneurysms.

In addition, the software measures the size of the retinal hemorrhages, exudates or aneurysms. The actual computation is performed remotely by computers to which the smartphone app connects through the cloud. The macro-phases of the workflow performed to carry out these measurements are the following (FIG. 5).

A. Identification of the Optic Nerve

The retinal image acquired by means of the system previously described is transformed into a monochromatic image. Then, the application of the Variance filter enclosed in the freeware, open source ImageJ software package (http://rsbweb.nih.gov/ij/) allows the main retinal structures (i.e. the optic nerve and the retinal vessels) to emerge from the background of the retinal image. The resulting image is then transformed into a binary image, which will show black pixels that correspond to the optic nerves and retinal vessels, and white pixels that correspond to the background. The software then automatically identifies the optical nerve in the best circular shape pattern within the image.

A.1 Transformation of the acquired retinal image into a monochromatic image by splitting the RGB image into the 3 channels corresponding to each primary color (red, green, blue), and selection of the green channel for the analysis.

A.2 Multiple iterations of the Variance filter using incremental contrast values, in order to enhance the contrast between the optic nerve and the background of the retinal image.

A.3 Transformation of the filtered monochromatic image into a binary image. The resulting image will show black pixels corresponding to the main retinal anatomic structures (i.e. the optic nerve and the retinal vessels), and white pixels corresponding to the background. Based on the relative amount of the black pixels, multiple iterations of the Variance filter (step A.2) will be performed, according to the following rule: if the number of black pixels is less than 10% of the total number of pixels, the filtering (step A.2) is executed over again upon incrementing the contrast value by 20 units (in a conventional contrast scale ranging from 1 to 256).

A.4 Automated detection of the optic nerve within the binary image, based on the following criteria: 1) circular shape; 2) circumference value equal to or greater than a given threshold, say CT, of pixels. An ad hoc algorithm looks for the best circular shape within the binary image which has a radius of at least CTpx. Once this region is identified, its size and coordinates will allow to locate the exact position of the optic nerve within the original image. In case of multiple candidate regions, the one showing the best fit to the criteria is selected.

A.5 Extrapolation of the coordinates of the center of the optic nerve, and measurement of its diameter. This step is critical to step E.2 (ROI selection for fractal analysis).

Identification of the optic nerve serves as template to perform the analyses targeting the optic nerve (step B), as well as to draw the region of interest (ROI) for fractal analysis (step E).

B. Detection of Optic Nerve Abnormalities

This step of the workflow automatically detects abnormalities concerning 1) the color, 2) the margins of the optic nerve identified through the previous step.

Color abnormalities in the optic nerve are identified by a) computing the average brightness across the whole image; b) computing the average brightness of the optic nerve; and c) comparing (a) with (b): a ratio average_brightness(optic_nerve)/average_brightness(whole_eye) greater than the one measured in a reference control group of healthy subjects is considered abnormal. Optic nerve size and shape are flagged as abnormal when the main algorithm fails to identify the optic nerve. The combination of these two features allows to perform automatic detection of optic nerve abnormalities, such as papilledema or optic neuritis. In fact, papilledema is characterized by blurred margins of the optic disc (abnormal size and shape of the optic disc); while pale color and well-defined margins of the optic disc are common features of optic neuritis.

The steps to detect optic nerve abnormalities are:

B.1 Detection of color abnormalities within the optic nerve, according to average brightness comparisons.

B.2 Computation of the margin swelling index obtained quantifying by what measure the main algorithm failed at precisely identifying a circular optic nerve.

B.3 Combination of the information obtained from steps B.1 and B.2 to compute likelihood indices for optic neuritis and papilledema.

C. Extraction of the Retinal Vessels

Extraction of the retinal vessels is based on multiple iterations of a background subtraction algorithm [5] that allows to isolate the elements of the retinal image corresponding to the vessels from the background of the retinal image acquired through the smartphone+lens system.

It includes the following sub-steps:

C.1 Inversion of the monochromatic output image of step A.1 (green channel) by transforming the black pixels into white pixels and vice versa, to obtain a negative copy of the monochromatic image.

C.2 Background subtraction from the negative (inverted) monochromatic image, according to the following sub-steps:

C.2-1 Multiple iterations of the Otsu thresholding algorithm, and record of the output thresholding value. If the thresholding value obtained from the first iteration of Otsu thresholding is ≥20 units (within a conventional contrast scale ranging from 1 to 256), a histogram equalization algorithm is executed to increase the contrast of the monochromatic image, and then the background subtraction step is performed over again. If the first thresholding value is <20 units (within a conventional contrast scale ranging from 1 to 256), the algorithm moves to step C.2-2.

C.2-2 Subtraction of the thresholding value from the image.

C.2-3 Transformation of the output image of step C.2-2 into a binary image.

C.3 Quality control of the output image of step C.2, according to the absolute cumulative number of continuous white pixels. If the cumulative number of white pixels is ≥10, the threshold value is subtracted from the image.

The resulting image constitutes the basis for the vessel tracking step.

D. Retinal Vessel Tracking

The A* "walking" algorithm [6] is exploited in order to obtain the basic parameters of the vessel geometry. Automatic retinal vessel tracking by means of skeletonization and automatic correction of interrupted vessel tracks are performed.

D.1 Skeletonization of the retinal vessels, which results in a representation of the vessels as lines of one-pixel thickness aligned to the center of each retinal vessels.

D.2 Filling the interrupted lines of the skeletonization output and reconstructing the path of the interrupted lines according to the following distance criterion. The number of pixels needed to reconnect two parts of a vessel is calculated by linear approximation.

D.3 Overlay the skeletonized image of the vessels with the original retinal image, to allow the user to select the retinal vessel segments to be analyzed. The user will select the start- and end-points of each vessel of interest. Based on the user selection, the app will provide visual feedback by highlighting the selected retinal vessel segments to be analyzed.

Once the retinal vessels have been tracked, the software provides a binary mask of the skeletonized vessels, which serves as input image for fractal analysis (step E). This binary mask is also overlaid to the original retinal image acquired through the smartphone+lens system to perform quantitative analyses targeting the retinal vessels (step F).

E. Fractal Analysis

FracLac (http://rsb.info.nih.gov/ii/plugins/frac-lac.html), a plugin for ImageJ, performs the fractal analysis of the retinal vascular tree using the box counting method. The input image is the binary mask of the skeletonized retinal vessels. To normalize for differences in eye size, a ROI uniform across the subjects is automatically selected. The radius of the optical nerve is adopted to select a circular ROI of 3.5× optic disc diameter, concentric with the optic nerve. The fractal analysis is performed on a cropped image including only the ROI.

The steps to perform fractal analysis are:

E.1 Use of the binary image of the skeletonized retinal vessels obtained from steps D.1 and D.2 as input images.

E.2 Selection of the ROI to be analyzed. Based on the results of step A, which identifies the optic nerve position and measures the optic nerve diameter, a circular ROI of 3.5× optic disc diameter, concentric with the optic nerve is selected;

E.3 Image cropping. The selected ROI is used to crop the binary image of the skeletonized retinal vessel.

E.4 Fractal analysis is performed by means of FracLac (http//rsb.info.nih.gov/ij/plugins/frac-lac.html), a plugin for ImageJ that computes the mean fractal dimension (Mean-D) index by box counting method.

F. Measurement of Retinal Vessel Diameter and Tortuosity (AVR and TI)

This step is devoted to the measurement of the diameter and tortuosity of the selected vessel segments. The user can select the start- and end-points of each vessel segment to be analyzed on a composite image of the retina overlaid with the skeletonized output of the vessel tracking. In order to measure the diameter of each vessel segment the shortest distance between the edges of the vessel is computed for each pixel along the segment length.

This step includes the following sub-steps:

F.1 Following the extraction of the track of the retinal vessels (steps C and D) and arbitrary selection of vessel segments by the user, the app produces a matrix of paired values. Each pair corresponds to the start- and end-points of each vessel segment. For each vessel segment the software computes the quantitative indices of retinal vessel damage.

F.2 Automated compiling of a list of all the selected start- and end-points within the skeletonized retinal vessels map, by means of an algorithm (A*) that uses as input the start- and end-points pairs and follows the path of each vessel pixel-by-pixel along the skeletonized lines.

F.3 Computation of the average diameter of each blood vessel segment, according to the following sub-steps:
  F.3-1 Calculating the number of the contiguous white pixels in the two directions of the cartesian axis and in the two directions at 45 deg with respect to the cartesian axes for each pixel of the skeletonized vessel segment.
  F.3-2 Choosing the smallest value among those obtained in step F.3-1 as diameter value relevant to each pixel.
  F.3-3 Carrying out the average of the diameter values obtained for each pixel.

F.4 Computation of the Arteriole-to-Venule diameter Ratio (AVR), according to the following formula $$AVR = \frac{d_a}{d_V}$$

Where $d_a$ is the average diameter of a given retinal artery and $d_v$ is the average diameter of a given retinal vein. The average diameter is obtained, pixel by pixel, from the image containing the extracted vessels, before the "Skeletonize" function is applied. For the purpose, the shortest distance between the edges of the vessel is computed for each pixel of the segment length. More in detail, each pixel is considered as the center of a square, and a search is performed, counting how many consecutive "white" pixels are found starting from such a center and looking horizontally, vertically, and diagonally. For each pixel i, the minimum value is taken as the value $width_i$. The average value among all pixels is then taken as diameter. If a given vessel counts N pixels, we have:

$$d = \frac{\sum_{i=1}^{N} width_i}{N}$$

F.5 Computation of the Tortuosity Index (TI). TI takes into account: 1) the area of the curve delineated by the vessel segment; 2) the number of directional changes along the vessel path, normalized by the total length of the selected vessel segment. The directional changes are defined as points where the first derivative of the analytical function is equal to zero, corresponding to the points where vessel path changes its slope. Specifically, TI is computed according to the following sub-steps:

F.5-1 The selected start- and end-points of the retinal vessel segment of interest are transformed into a new coordinate space in order to fit coordinates (0,0) for the start-point and coordinates (n,0) for the endpoint, where n is the length of the blood vessel.

F.5-2 Obtaining an analytical function ($f$) which represents the shape of the retinal vessels by using Bezier interpolation.

F.5-3 Let $d_0$ and $d_p$ respectively the first and the last point of the vessel and $d_i \in D (0 \leq i \leq p)$ where $D = \{x : f'(x) = 0\}$ and $d_i < di+1 \ \forall (0 \leq i \leq p)$, then TI is computed according to the following formula:

$$TI = \sum_{i=0}^{p-1} \frac{|f(d_i) - f(d_{i+1})|}{\sqrt{(d_i - d_{i+1})^2 + (f(d_i) - f(d_{i+1}))^2}}$$

G. Quantification of Retinal Hemorrhages, Exudates and Aneurysms

Automatic quantification of retinal hemorrhages, exudates and aneurysms through a threshold-based method G.1 Execution of the Remove outliers filter command enclosed in the ImageJ software package to identify spots with outlier signal intensity.

G.2 Extraction of outlier spots lead to a separate image and binarization of such image.

G.3 Computation of the total area of the obtained mask.

G.4 Option for the user to remove outliers in order to improve the performance of the background subtraction.

The Remove outliers filter enclosed in the ImageJ software package allows to identify spots with outlier signal intensity. Extracted outlier spots lead to a separate image; such image is then binarized, thus allowing to obtain the best visual fit to the retinal hemorrhage, exudate and aneurysm burden. Based on the binary mask, the total areas of the retinal hemorrhage, exudate and aneurysm burden is automatically computed.

H. Longitudinal Comparison

Automatic longitudinal comparison of the quantitative indices of retinal damage through spatial alignment of the retinal images and comparison of time series of images from the same subject. Longitudinal comparison of the indices of retinal damage are obtained by comparison of time series measurements from the same subject. Using a registration tool, the retinal images from different time points are aligned to each other. The procedure allows to monitor potential changes of the quantitative indices of retinal damage, during repeated measurements along a defined time period.

H.1 Alignment of the different retinal images using an Affine registration algorithm.

H.2 Computation of the quantitative indices of retinal damage corresponding to each time point, according to the workflow steps C to G.

H.3 Tabulation of the results for comparison. The user has the option to select the reference image for longitudinal analysis.

The invention claimed is:

1. Portable, medical device to acquire retinal images and perform quantitative retinal image analysis consisting of a smartphone having a photo camera and a light source, a macro lens and a refractor wherein both the macro lens and the refractor are mounted on a detachable element that fits the smartphone, and further the macro lens is calibrated to focus on the posterior surface of the eye and the refractor is positioned to face the light source of the smartphone, wherein the light coming from the light source of the smartphone gets into the refractor and the refracted light gathers through the corneal window into the pupil of a person and shines the inner posterior surface of the eye bulb, corresponding to the retina, wherein the smartphone acquires a retinal image when the posterior surface of the eye is illuminated by the light source of the smartphone refracted by the refractor and focused by the macro lens, and wherein through an app the acquired retinal image is analyzed to carry out quantitative indices of retinal damage.

2. Portable medical device to acquire retinal images and perform quantitative retinal image analysis according to claim 1 wherein the detachable element is an adjustable band.

3. Portable medical device to acquire retinal images and perform quantitative retinal image analysis according to claim 2 wherein the macro lens and the refractor are mounted on a sliding track present on the adjustable band.

4. Portable medical device to acquire retinal images and perform quantitative retinal image analysis according to claim 2 wherein the band has a circular shape, it is semi-flexible and is made of plastic or rubber.

5. Portable medical device to acquire retinal images and perform quantitative retinal image analysis according to claim 2, wherein the refractor includes two rectangular parallel mirrors, which are positioned at 45 degree angle with respect to the axis perpendicular to the surface of the refractor, and the refractor has two holes—an input hole that allows the light coming from the smartphone light source to get into the refractor and an output hole that allows the refracted light to gather through the corneal window into the pupil and shine the inner posterior surface of the eye bulb, corresponding to the retina.

6. Portable medical device to acquire retinal images and perform quantitative retinal image analysis according to claim 1, wherein the refractor includes two rectangular parallel mirrors, which are positioned at 45 degree angle with respect to the axis perpendicular to the surface of the refractor, and the refractor has two holes—an input hole that allows the light coming from the smartphone light source to get into the refractor and an output hole that allows the refracted light to gather through the conical window into the pupil and shine the inner posterior surface of the eye bulb, corresponding to the retina.

7. Method to acquire retinal images and perform quantitative retinal image analysis through the portable medical device of claim 1, wherein through a smartphone app
   a. optic nerve is automatically identified through geometric shape search and techniques for image color reduction;
   b. abnormalities of optic nerve are detected by means of its color, brightness and shape analysis;
   c. retinal vessel are automatically extracted by means of background subtraction techniques;
   d. retinal vessels are automatically tracked by means of skeletonization and an on-purpose algorithm; possible interrupted lines are fixed and the path of interrupted lines is reconstructed by means of linear approximation;
   e. skeletonized retinal vessels are automatically analyzed via a fractal measure within an automatically selected region of interest;
   f. retinal vessel diameter and tortuosity of manually or automatically selected retinal vessel segments are automatically measured;
   g. retinal hemorrhages, exudates and aneurysms are automatically quantified by means of a threshold-based method;
   h. an automatic longitudinal comparison of the quantitative indices of retinal damage, as computed at different time points per each subject, is performed through spatial alignment of the retinal images and comparison of time series of images from the same subject.

8. Method to acquire retinal images and perform quantitative retinal image analysis through a portable medical device according to claim 7 wherein the automatic identification of the optic nerve is made through:
   A.1 transformation of the acquired retinal image into a monochromatic image by splitting the RGB image into the 3 channels corresponding to each primary color, and selection of the green channel image for the analysis;
   A.2 multiple iterations of a known variance filter using incremental contrast values, in order to enhance the contrast between the optic nerve and the background of the retinal image;
   A.3 transformation of the filtered monochromatic image into a binary image; the resulting image will show black pixels corresponding to the main retinal anatomic structures, and white pixels corresponding to the background; based on the relative amount of the black pixels, multiple iterations of the variance filter will be performed, according to the following rule: if the number of black pixels is less than 10% of the total number of pixels, filtering through the variance filter is executed over again upon incrementing the contrast values by 20 units in a conventional contrast scale ranging from 1 to 256;
   A.4 automated detection of the optic nerve within the binary image, based on the following criteria: 1) circular shape; 2) circumference value equal to or greater than a given threshold CT, of pixels, an ad hoc algorithm looks for the best resembling of a circular shape pattern within the binary image, which has a radius of at least CTpx, once this region is identified, its size and coordinates will allow to locate the exact position of the optic nerve within the original image; in case of multiple candidate regions, the one showing the best fit to the criteria is selected;
   A.5 extrapolation of the coordinates of the center of the optic nerve, and measurement of its diameter.

9. Method to acquire retinal images and perform quantitative retinal image analysis through a portable medical device according to claim 8 wherein automatic detection of optic nerve abnormalities is made through:
   B.1 detection of color abnormalities within the optic nerve, according to average brightness comparisons;
   B.2 computation of the margin swelling index obtained by quantifying the thickness of the borders of the optic nerve; the optic nerve border thickness is computed as the square root of the difference between the area of the optic nerve and the smallest circle that contains it;

B.3 combination of the information obtained from steps B.1 and B.2 to compute likelihood indices for optic neuritis and papilledema.

10. Method to acquire retinal images and perform quantitative retinal image analysis through a portable medical device according to claim 9 wherein automatic extraction of the retinal vessels is made through:

C.1 inversion of the monochromatic output image of step A.1 by transforming the black pixels into white pixels and vice versa, to obtain a negative copy of the monochromatic image;

C.2 background subtraction from the negative monochromatic image, according to the following sub-steps:

C.2-1 multiple iterations of the Otsu thresholding algorithm, and record of the output thresholding value; if the thresholding value obtained from the iteration of Otsu thresholding is ≥20 units within a conventional contrast scale ranging from 1 to 256, a histogram equalization algorithm is executed to increase the contrast of the monochromatic image, and then the background subtraction step is performed over again; if the output Otsu thresholding value is <20 units within said conventional contrast scale ranging from 1 to 256, the algorithm moves to step C.2-2;

C.2-2 subtraction of the thresholding value obtained in C.2-1 from the image;

C.2-3 transformation of the output image of step C.2-2 into a binary image;

C.3 Quality control of the output image of step C.2, according to the absolute cumulative number of continuous white pixels; if the cumulative number of white pixels is ≥10 the threshold value is subtracted from the image.

11. Method to acquire retinal images and perform quantitative retinal image analysis through a portable medical device according to claim 10 wherein automatic retinal vessel tracking and automatic correction of interrupted vessel tracks are made through:

D.1 skeletonization of the retinal vessels, which results in a representation of the vessels as lines of one-pixel thickness aligned to the center of each retinal vessel;

D.2 filling the interrupted lines of the skeletonization output and reconstructing the path of the interrupted lines according to the following distance criterion, the number of pixels needed to reconnect two parts of a vessel is calculated by linear approximation;

D.3 overlay the skeletonized image of the vessels with the original retinal image, to allow the user to select the retinal vessel segments to be analyzed, the user will select the start- and end-points of each vessel of interest, based on the user selection, the app will provide visual feedback by highlighting the selected retinal vessel segments to be analyzed.

12. Method to acquire retinal images and perform quantitative retinal image analysis through a portable medical device according to claim 11 wherein automatic fractal analysis of skeletonized retinal vessels is made through:

E.1 use of the binary image of the skeletonized retinal vessels obtained from steps D.1 and D.2 as input image;

E.2 selection of the ROI to be analyzed; based on the results of step A, which identifies the optic nerve position and measures the optic nerve diameter, it is selected a circular ROI of a multiple of the optic disc diameter in size, concentric with the optic nerve;

E.3 image cropping; the selected ROI is used to crop the binary image of the skeletonized retinal vessel;

E.4 fractal analysis is performed by means of FracLac, a plugin for ImageJ that computes the mean fractal dimension, Mean-D, index by box counting method.

13. Method to acquire retinal images and perform quantitative retinal image analysis through a portable medical device according to claim 12 wherein automatic measurement of retinal vessel diameter and tortuosity is made through F.1 following extraction of the track of the retinal vessels (steps C and D) and arbitrary selection of vessel segments by the user, the app produces a matrix of paired values, each pair corresponds to the start- and end-points of each vessel segment, for each vessel segment the software computes the quantitative indices of retinal vessel damage;

F.2 automated compiling of a list of all the selected start- and end-points within the skeletonized retinal vessels map, by means of an algorithm (A*) that uses as input the start- and end-points pairs and follows the path of each vessel pixel-by-pixel along the skeletonized lines;

F.3 computation of the average diameter of each blood vessel segment, according to the following sub-steps:

F.3-1 calculating the number of the contiguous white pixels in the two directions of the cartesian axis and in the two directions at 45 degrees with respect to the cartesian axes for each pixel of the skeletonized vessel segment;

F.3-2 choosing the smallest value among those obtained in the directions of step F.3-1 as diameter value relevant to each pixel;

F.3-3 carrying out the average of the diameter values obtained for each pixel; this average is assigned as average vessel diameter;

F.4 computation of the Arteriole-to-Venule diameter Ratio (AVR), according to the following formula $$AVR = \frac{d_a}{d_V}$$

where $d_a$ is the average diameter of a given artery and $d_v$ is the average diameter of a given vein segment, the average diameter is obtained, pixel by pixel, from the image containing the extracted vessels, before the Skeletonize is applied, for the purpose, the shortest distance between the edges of the vessel is computed for each pixel of the segment length, were each pixel is considered as the center of a square, and a search is performed, counting how many consecutive "white" pixels are found starting from such a center and looking horizontally, vertically, diagonally and where for each pixel i, the minimum value is taken as the value $width_i$, the average value among all pixels is then taken for final result as average diameter of the vessel, if a given vessel counts N pixels, we have:

$$d = \frac{\sum_{i=1}^{N} width_i}{N}$$

F.5 computation of the Tortuosity Index (TI), according to the following sub-steps:

F.5-1 each vessel undergoes a distortion-free rotation, so that both the start- and end-point lay on the x-axis: the selected start- and end-points of the retinal vessel segment of interest, as well as all the points in between, are transformed into a new coordinate space in order to fit coordinates (0,0) for the start-point and coordinates (n,0) for the endpoint where n is the length of the vessel;

F.5-2 obtaining an analytical function CO which represents the shape of the retinal vessel by using a Bezier interpolation;

F.5-3 let $d_0$ and $d_p$ respectively the start and the end point of the vessel and $d_i \epsilon D(0 \leq i \leq p)$ where $D=\{x:f'(x)=0\}$; and $d_i < d_i+1$ $\forall (0 \leq i \leq p)$, then TI is computed according to the following formula:

$$TI = \sum_{i=0}^{p-1} \frac{|f(d_i) - f(d_{i+1})|}{\sqrt{(d_i - d_{i+1})^2 + (f(d_i) - f(d_{i+1}))^2}}$$

14. Method to acquire retinal images and perform quantitative retinal image analysis through a portable medical device according to claim 13 wherein automatic quantification of retinal hemorrhages, exudates and aneurysms is made through G.1 execution of the Remove outliers filter command enclosed in imageJ software package to identify spots with outlier signal intensity;

G.2 extraction of outlier spots lead to a separate image and binarization of such image;

G.3 computation of the total area of the mask obtained through the previous steps;

G.4 option for the user to remove outliers in order to improve the performance of the background subtraction.

15. Method to acquire retinal images and perform quantitative retinal image analysis through a portable medical device according to claim 7 wherein automatic longitudinal comparison of the quantitative indices of retinal damage is made through:

H.1 alignment of the different retinal images using an Affline registration algorithm;

H.2 computation of the quantitative indices of retinal damage corresponding to each time point, according to the steps C to G;

H.3 tabulation of the results for comparison where user has the option to select the reference image for the longitudinal analysis.

* * * * *